(12) United States Patent
Möckel et al.

(10) Patent No.: US 6,987,015 B1
(45) Date of Patent: Jan. 17, 2006

(54) NUCLEOTIDE SEQUENCES ENCODING THE PFKA GENE

(75) Inventors: Bettina Möckel, Düsseldorf (DE); Walter Pfefferle, Halle (DE)

(73) Assignee: Degussa AG, Dusseldorf (DE)

( * ) Notice: Subject to any disclaimer, the term of this patent is extended or adjusted under 35 U.S.C. 154(b) by 422 days.

(21) Appl. No.: 09/715,035

(22) Filed: Nov. 20, 2000

(30) Foreign Application Priority Data

Nov. 23, 1999 (DE) ......................................... 199 56 133

(51) Int. Cl.
   *C12N 9/12* (2006.01)

(52) U.S. Cl. .................. 435/194; 435/183; 435/252.3; 435/252.32; 435/320.1; 536/23.2

(58) Field of Classification Search ................ 435/183, 435/194, 252.3, 252.32, 320.1; 536/23.2
   See application file for complete search history.

(56) References Cited

U.S. PATENT DOCUMENTS

2002/0068335 A1    6/2002   Thierbach et al. ........... 435/106

FOREIGN PATENT DOCUMENTS

| EP | 0 108 790   | 6/2001 |
| EP | 1 167 520   | 1/2002 |
| EP | 1 195 431   | 4/2002 |
| EP | 1 219 712   | 7/2002 |
| WO | WO 02/074944 | 9/2002 |

OTHER PUBLICATIONS

Attwood et al. Which craft is best in bioinformatics? Comput. Chem. 2001, Vol. 25(4), pp. 329–339.*
Ponting, C.P. Issues in predicting protein function from sequence. Brief Bioinform. Mar. 2001, vol. 2(1), pp. 19–29.*
Hirano et al. Accession AB083051. Apr. 03, 2002.*
Oliver et al. Accession Z99263. Sep. 17, 1997 (Alignmnet No. 1).*
Parkhill et al., "Use of an Ordered Cosmid Library to Deduce the Genomic Organization of Mycobacterium Leprae," *Molecular Microbiology*, vol. 7, No. 2, 1993, pp. 197–206.
Database EMBL; Accesion No. AL022374; XP002189182.
Database WPI; Accession No. XP002189183.
Kramer, "Genetic and physiological approaches for the production of amino acids", Journal of Biotechnology, vol. 45, No. 1, pp. 1–21.
Eikmanns et al., "Molecular aspects of lysine, threonine, and isoleucine biosynthesis in Corynebacterium glutamicum", Antonie Van Leeuwenhoek, vol. 64, No. 2, pp. 145–163.

* cited by examiner

*Primary Examiner*—Tekchand Saidha
*Assistant Examiner*—Christian L. Fronda
(74) *Attorney, Agent, or Firm*—Pillsbury Winthrop LLP

(57) ABSTRACT

An isolated polynucleotide containing a polynucleotide sequence selected from the following group:
   a) a polynucleotide which is at least 70% identical to a polynucleotide which codes for a polypeptide containing the amino acid sequence of SEQ ID NO:2,
   b) a polynucleotide which encodes a polypeptide which contains an amino acid sequence which is at least 70% identical to the amino acid sequence of SEQ ID NO:2,
   c) a polynucleotide which is complementary to the polynucleotides of a) or b), and
   d) a polynucleotide containing at least 15 successive nucleotides of the polynucleotide sequence of a), b) or c), a process for the fermentative production of L-amino acids with amplification of the pfkA gene and use as primer or hybridisation probe.

9 Claims, 2 Drawing Sheets

Figur 1: Plasmidkarte pT-pfkAexp
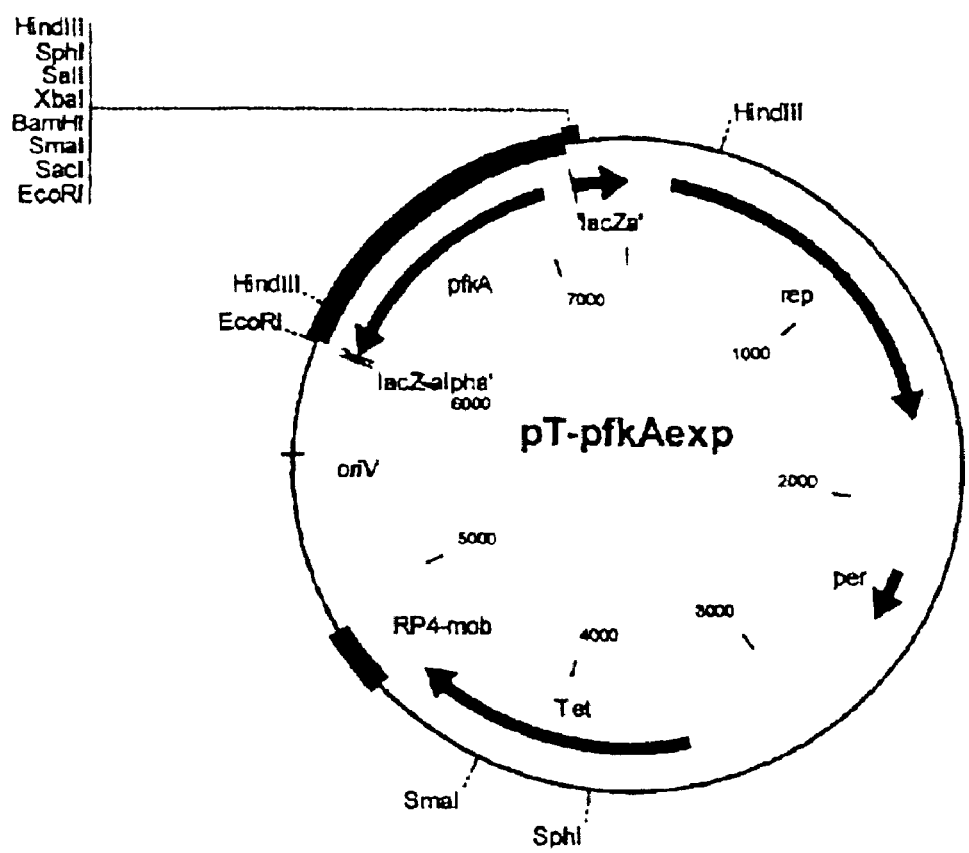

Figure 2: Plasmid map of pT-pfkAexp
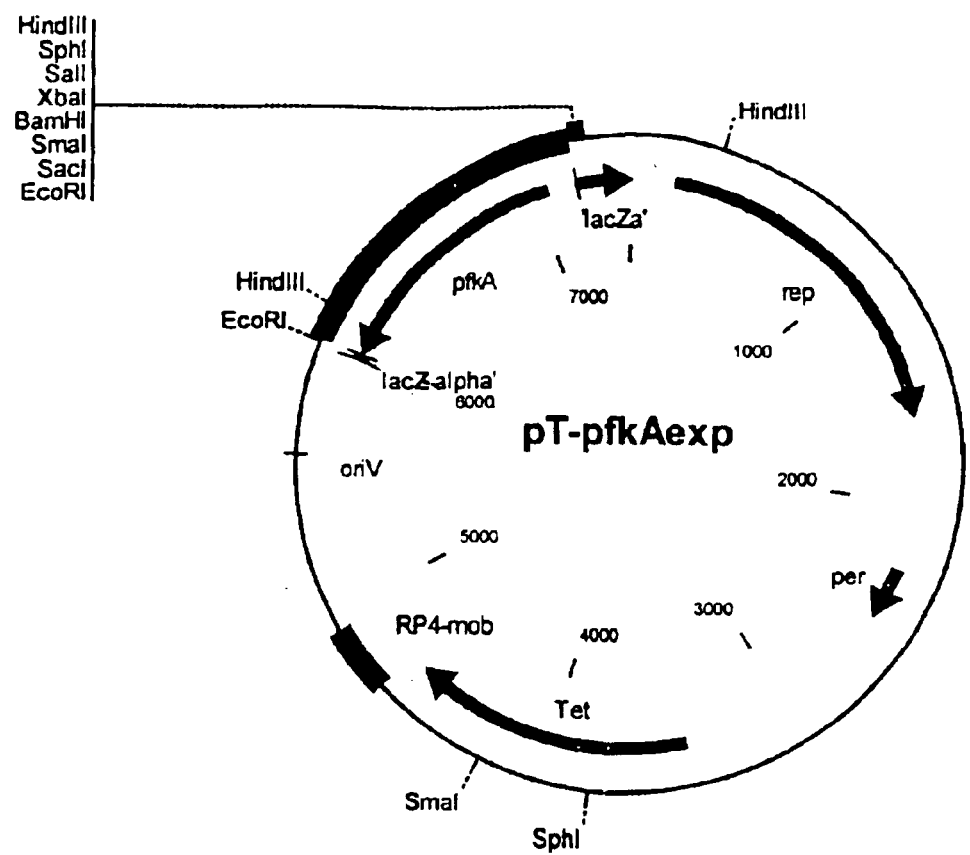

SEQUENCE LISTING

<160> NUMBER OF SEQ ID NOS: 4

<210> SEQ ID NO 1
<211> LENGTH: 1274
<212> TYPE: DNA
<213> ORGANISM: Corynebacterium glutamicum
<220> FEATURE:
<221> NAME/KEY: CDS
<222> LOCATION: (143)..(1171)

<400> SEQUENCE: 1

```
gtcgatttgt taatgaaact gcagctctgg cgattaaata agatggtcag agacagtttt      60
ttggcctgtc aaccctgtg attctcttat ttttgggtga ttgttccggc gcgggtgttg     120
tgatgggttt aatatggaag ac atg cga att gct act ctc acg tca ggc ggc    172
                        Met Arg Ile Ala Thr Leu Thr Ser Gly Gly
                         1               5                  10 gac tgc ccc gga cta aac gcc gtc atc cga gga atc gtc cgc aca gcc    220
Asp Cys Pro Gly Leu Asn Ala Val Ile Arg Gly Ile Val Arg Thr Ala
             15                  20                  25 agc aat gaa ttt ggc tcc acc gtc gtt ggt tat caa gac ggt tgg gaa    268
Ser Asn Glu Phe Gly Ser Thr Val Val Gly Tyr Gln Asp Gly Trp Glu
         30                  35                  40 gga ctg tta ggc gat cgt cgc gta cag ctg tat gac gat gaa gat att    316
Gly Leu Leu Gly Asp Arg Arg Val Gln Leu Tyr Asp Asp Glu Asp Ile
     45                  50                  55 gac cga atc ctc ctt cga ggc ggc acc att ttg ggc act ggt cgc ctc    364
Asp Arg Ile Leu Leu Arg Gly Gly Thr Ile Leu Gly Thr Gly Arg Leu
 60                  65                  70 cat ccg gac aag ttt aag gcc gga att gat cag att aag gcc aac tta    412
His Pro Asp Lys Phe Lys Ala Gly Ile Asp Gln Ile Lys Ala Asn Leu
 75                  80                  85                  90 gaa gac gcc ggc atc gat gcc ctt atc cca atc ggt ggc gaa gga acc    460
Glu Asp Ala Gly Ile Asp Ala Leu Ile Pro Ile Gly Gly Glu Gly Thr
                 95                 100                 105 ctg aag ggt gcc aag tgg ctg tct gat aac ggt atc cct gtt gtc ggt    508
Leu Lys Gly Ala Lys Trp Leu Ser Asp Asn Gly Ile Pro Val Val Gly
            110                 115                 120 gtc cca aag acc att gac aat gac gtg aat ggc act gac ttc acc ttc    556
Val Pro Lys Thr Ile Asp Asn Asp Val Asn Gly Thr Asp Phe Thr Phe
        125                 130                 135 ggt ttc gat act gct gtg gca gtg gct acc gac gct gtt gac cgc ctg    604
Gly Phe Asp Thr Ala Val Ala Val Ala Thr Asp Ala Val Asp Arg Leu
    140                 145                 150 cac acc acc gct gaa tct cac aac cgt gtg atg atc gtg gag gtc atg    652
His Thr Thr Ala Glu Ser His Asn Arg Val Met Ile Val Glu Val Met
155                 160                 165                 170 ggc cgc cac gtg ggt tgg att gct ctg cac gca ggt atg gcc ggc ggt    700
Gly Arg His Val Gly Trp Ile Ala Leu His Ala Gly Met Ala Gly Gly
                175                 180                 185 gct cac tac acc gtt att cca gaa gta cct ttc gat att gca gag atc    748
Ala His Tyr Thr Val Ile Pro Glu Val Pro Phe Asp Ile Ala Glu Ile
            190                 195                 200 tgc aag gcg atg gaa cgt cgc ttc cag atg ggc gag aag tac ggc att    796
Cys Lys Ala Met Glu Arg Arg Phe Gln Met Gly Glu Lys Tyr Gly Ile
        205                 210                 215 atc gtc gtt gcg gaa ggt gcg ttg cca cgc gaa ggc acc atg gag ctt    844
Ile Val Val Ala Glu Gly Ala Leu Pro Arg Glu Gly Thr Met Glu Leu
    220                 225                 230
```

```
cgt gaa ggc cac att gac cag ttc ggt cac aag acc ttc acg gga att       892
Arg Glu Gly His Ile Asp Gln Phe Gly His Lys Thr Phe Thr Gly Ile
235                 240                 245                 250 gga cag cag atc gct gat gag atc cac gtg cgc ctc ggc cac gat gtt       940
Gly Gln Gln Ile Ala Asp Glu Ile His Val Arg Leu Gly His Asp Val
                255                 260                 265 cgt acg acc gtt ctt ggc cac att caa cgt ggt gga acc cca act gct       988
Arg Thr Thr Val Leu Gly His Ile Gln Arg Gly Gly Thr Pro Thr Ala
            270                 275                 280 ttc gac cgt gtt ctg gcc act cgt tat ggt gtt cgt gca gct cgt gcg      1036
Phe Asp Arg Val Leu Ala Thr Arg Tyr Gly Val Arg Ala Ala Arg Ala
        285                 290                 295 tgc cat gag gga agc ttt gac aag gtt gtt gct ttg aag ggt gag agc      1084
Cys His Glu Gly Ser Phe Asp Lys Val Val Ala Leu Lys Gly Glu Ser
    300                 305                 310 att gag atg atc acc ttt gaa gaa gca gtc gga acc ttg aag gaa gtt      1132
Ile Glu Met Ile Thr Phe Glu Glu Ala Val Gly Thr Leu Lys Glu Val
315                 320                 325                 330 cca ttc gaa cgc tgg gtt act gcc cag gca atg ttt gga tagttttcg        1181
Pro Phe Glu Arg Trp Val Thr Ala Gln Ala Met Phe Gly
                335                 340 ggctttttatc aacagccaat aacagctctt tcgcccattg aggtggaggg ctgtttttt    1241 catgccgtaa ggaaagtgca agtaagtgaa atc                                  1274

<210> SEQ ID NO 2
<211> LENGTH: 343
<212> TYPE: PRT
<213> ORGANISM: Corynebacterium glutamicum

<400> SEQUENCE: 2

Met Arg Ile Ala Thr Leu Thr Ser Gly Gly Asp Cys Pro Gly Leu Asn
1               5                   10                  15

Ala Val Ile Arg Gly Ile Val Arg Thr Ala Ser Asn Glu Phe Gly Ser
                20                  25                  30

Thr Val Val Gly Tyr Gln Asp Gly Trp Glu Gly Leu Leu Gly Asp Arg
            35                  40                  45

Arg Val Gln Leu Tyr Asp Asp Glu Asp Ile Asp Arg Ile Leu Leu Arg
        50                  55                  60

Gly Gly Thr Ile Leu Gly Thr Gly Arg Leu His Pro Asp Lys Phe Lys
65                  70                  75                  80

Ala Gly Ile Asp Gln Ile Lys Ala Asn Leu Glu Asp Ala Gly Ile Asp
                85                  90                  95

Ala Leu Ile Pro Ile Gly Gly Glu Gly Thr Leu Lys Gly Ala Lys Trp
            100                 105                 110

Leu Ser Asp Asn Gly Ile Pro Val Val Gly Val Pro Lys Thr Ile Asp
        115                 120                 125

Asn Asp Val Asn Gly Thr Asp Phe Thr Phe Gly Phe Asp Thr Ala Val
    130                 135                 140

Ala Val Ala Thr Asp Ala Val Asp Arg Leu His Thr Thr Ala Glu Ser
145                 150                 155                 160

His Asn Arg Val Met Ile Val Glu Val Met Gly Arg His Val Gly Trp
                165                 170                 175

Ile Ala Leu His Ala Gly Met Ala Gly Ala His Tyr Thr Val Ile
            180                 185                 190

Pro Glu Val Pro Phe Asp Ile Ala Glu Ile Cys Lys Ala Met Glu Arg
        195                 200                 205
```

-continued

```
Arg Phe Gln Met Gly Glu Lys Tyr Gly Ile Ile Val Val Ala Glu Gly
    210                 215                 220

Ala Leu Pro Arg Glu Gly Thr Met Glu Leu Arg Glu Gly His Ile Asp
225                 230                 235                 240

Gln Phe Gly His Lys Thr Phe Thr Gly Ile Gly Gln Gln Ile Ala Asp
                245                 250                 255

Glu Ile His Val Arg Leu Gly His Asp Val Arg Thr Thr Val Leu Gly
            260                 265                 270

His Ile Gln Arg Gly Gly Thr Pro Thr Ala Phe Asp Arg Val Leu Ala
        275                 280                 285

Thr Arg Tyr Gly Val Arg Ala Arg Ala Cys His Glu Gly Ser Phe
290                 295                 300

Asp Lys Val Val Ala Leu Lys Gly Glu Ser Ile Glu Met Ile Thr Phe
305                 310                 315                 320

Glu Glu Ala Val Gly Thr Leu Lys Glu Val Pro Phe Glu Arg Trp Val
                325                 330                 335

Thr Ala Gln Ala Met Phe Gly
            340

<210> SEQ ID NO 3
<211> LENGTH: 20
<212> TYPE: DNA
<213> ORGANISM: PCR primer

<400> SEQUENCE: 3
aactgcagct ctggcgatta                                                 20

<210> SEQ ID NO 4
<211> LENGTH: 20
<212> TYPE: DNA
<213> ORGANISM: PCR primer

<400> SEQUENCE: 4
aactatccaa acattgcctg                                                 20
```

NUCLEOTIDE SEQUENCES ENCODING THE PFKA GENE

This application claims priority from German Application Nos. 199 56 133.8, filed on Nov. 23, 1999, and 100 11 922.0 filed Mar. 11, 2000, the subject matter of each of which is hereby incorporated herein by reference.

BACKGROUND OF THE INVENTION

1. Field of the Invention

The present invention provides nucleotide sequences coding for the pfka gene and a process for the fermentative production of L-amino acids, in particular L-lysine, using coryneform bacteria in which the pfka gene is amplified.

2. Background Information

Amino acids, in particular L-lysine, are used in human medicine and in the pharmaceuticals industry, but in particular in animal nutrition.

It is known that amino acids are produced by fermentation of strains of coryneform bacteria, in particular *Corynebacterium glutamicum*. Due to their great significance, efforts are constantly being made to improve the production process. Improvements to the process may relate to measures concerning fermentation technology, for example stirring and oxygen supply, or to the composition of the nutrient media, such as for example sugar concentration during fermentation, or to working up of the product by, for example, ion exchange chromatography, or to the intrinsic performance characteristics of the microorganism itself.

The performance characteristics of these microorganisms are improved using methods of mutagenesis, selection and mutant selection. In this manner, strains are obtained which are resistant to antimetabolites, such as for example the lysine analogue S-(2-aminoethyl)cysteine, or are auxotrophic for regulatorily significant metabolites and produce L-amino acids, such as for example L-lysine.

For some years, methods of recombinant DNA technology have likewise been used to improve strains of Corynebacterium which produce amino acids by amplifying individual biosynthesis genes and investigating the effect on amino acid production. Review articles on this subject may be found inter alia in Kinoshita ("Glutamic Acid Bacteria", in: Biology of Industrial Microorganisms, Demain and Solomon (Eds.), Benjamin Cummings, London, UK, 1985, 115–142), Hilliger (BioTec 2, 40–44 (1991)), Eggeling (Amino Acids 6:261–272 (1994)), Jetten and Sinskey (Critical Reviews in Biotechnology 15, 73–103(1995)) and Sahm et al. (Annuals of the New York Academy of Science 782, 25–39(1996)).

SUMMARY OF THE INVENTION

Object of the Invention

It is an object of of the invention to provide novel means for the improved fermentative production of amino acids, in particular L-lysine.

Description of the Invention

Amino acids, in particular L-lysine, are used in human medicine, in the pharmaceuticals industry and in particular in animal nutrition. There is accordingly general interest in providing novel improved processes for the production of amino acids, in particular L-lysine.

Any subsequent mention of L-lysine or lysine should be understood to mean not only the base, but also salts, such as for example lysine monohydrochloride or lysine sulfate.

The invention provides an isolated polynucleotide from coryneform bacteria containing a polynucleotide sequence selected from the group.

a) a polynucleotide which is at least 70% identical to a polynucleotide which encodes a polypeptide containing the amino acid sequence of SEQ ID NO:2, b) a polynucleotide which encodes a polypeptide which contains an amino acid sequence which is at least 70% identical to the amino acid sequence of SEQ ID NO:2, c) a polynucleotide which is complementary to the polynucleotides of a) or b), and d) polynucleotide containing at least 15 successive nucleotides of the polynucleotide sequence of a), b) or c).

The present invention also provides a polynucleotide with the features noted above, and comprising replicable DNA containing:

(i) the nucleotide sequence shown in SEQ ID NO:1, or (ii) at least one sequence which matches sequence (i) within the degeneration range of the genetic code, or (iii) at least one sequence which hybridises with the complementary sequence to sequence (i) or (ii) and optionally (iv) functionally neutral sense mutations in (i).

The present invention also provides a polynucleotide with the aforementioned features, containing the nucleotide sequence as shown in SEQ ID NO:1, a polynucleotide that is a replicable DNA with feature(s) of a)–d) that encodes a polypeptide which contains the amino acid sequence as shown in SEQ ID NO:2, a vector containing the polynucleotide with feature(s) of a)–d), in particular a shuttle vector or plasmid vector and coryneform bacteria acting as host cell which contain the vector.

The present invention also provides polynucleotides which substantially consist of a polynucleotide sequence, which are obtainable by screening by means of hybridisation of a suitable gene library, which contains the complete gene having the polynucleotide sequence according to SEQ ID NO:1, with a probe which contains the sequence of the stated polynucleotide according to SEQ ID NO:1, or a fragment thereof, and isolation of the stated DNA sequence.

Polynucleotide sequences according to the invention are suitable as hybridisation probes for RNA, cDNA and DNA in order to isolate full length cDNA which code for phosphofructokinase and to isolate such cDNA or genes, the sequence of which exhibits a high level of similarity with that of the phosphofructokinase gene.

Polynucleotide sequences according to the invention are furthermore suitable as primers for the production of DNA of genes which code for phosphofructokinase by the polymerase chain reaction (PCR).

Such oligonucleotides acting as probes or primers contain at least 30, preferably at least 20, very particularly preferably at least 15 successive nucleotides. Oligonucleotides having a length of at least 40 or 50 nucleotides are also suitable.

"Isolated" means separated from its natural environment.

"Polynucleotide" generally relates to polyribonucleotides and polydeoxyribonucleotides, wherein the RNA or DNA may be unmodified or modified.

"Polypeptides" are taken to mean peptides or proteins which contain two or more amino acids connected by peptide bonds.

The polypeptides according to the invention include a polypeptide according to SEQ ID NO:2, in particular those having the biological activity of phosphofructokinase and also those which are at least 70%, preferably at least 80%, identical to the polypeptide according to SEQ ID NO:2 and in particular are 90% to 95% identical to the polypeptide according to SEQ ID NO:2 and exhibit the stated activity.

The invention furthermore relates to a process for the fermentative production of amino acids, in particular L-lysine, using coryneform bacteria, which in particular already produce an amino acid and in which the nucleotide sequences which code for the pfkA gene are amplified, in particular overexpressed.

In this connection, the term "amplification" describes the increase in the intracellular activity of one or more enzymes in a microorganism, which enzymes are encoded by the corresponding DNA, for example by increasing the copy number of the gene or genes, by using a strong promoter or a gene which encodes a corresponding enzyme having elevated activity and optionally by combining these measures.

The microorganisms provided by the present invention may produce L-amino acids, in particular L-lysine, from glucose, sucrose, lactose, fructose, maltose, molasses, starch, cellulose or from glycerol and ethanol. The microorganisms may comprise representatives of the coryneform bacteria in particular of the genus Corynebacterium. Within the genus Corynebacterium, the species *Corynebacterium glutamicum* may in particular be mentioned, which is known in specialist circles for its ability to produce L-amino acids.

Suitable strains of the genus Corynebacterium, in particular of the species *Corynebacterium glutamicum*, are for example the known wild type strains

*Corynebacterium glutamicum* ATCC13032
*Corynebacterium acetoglutamicum* ATCC15806
*Corynebacterium acetoacidophilum* ATCC13870
*Corynebacterium thermoaminogenes* FERM BP-1539
*Corynebacterium melassecola* ATCC17965
*Brevibacterium flavum* ATCC14067
*Brevibacterium lactofermentum* ATCC13869 and
*Brevibacterium divaricatum* ATCC14020 and L-lysine producing mutants or strains produced therefrom, such as for example

*Corynebacterium glutamicum* FERM-P 1709
*Brevibacterium flavum* FERM-P 1708
*Brevibacterium lactofermentum* FERM-P 1712
*Corynebacterium glutamicum* FERM-P 6463
*Corynebacterium glutamicum* FERM-P 6464 and
*Corynebacterium glutamicum* DSM5715.

The inventors succeeded in isolating the novel pfkA gene, which codes for the enzyme phosphofructokinase (EC 2.7.1.11), from *C. glutamicum*.

The pfkA gene and other genes from *C. glutamicum* are isolated by initially constructing a gene library of this microorganism in *E. coli*. The construction of gene libraries is described in generally known textbooks and manuals. Examples which may be mentioned are the textbook by Winnacker, Gene und Klone, Eine Einführung in die Gentechnologie (Verlag Chemie, Weinheim, Germany, 1990) or the manual by Sambrook et al., Molecular Cloning, A Laboratory Manual (Cold Spring Harbor Laboratory Press, 1989). One very well known gene library is that of *E. coli* K-12 strain W3110, which was constructed by Kohara et al. (Cell 50, 495–508 (1987)) in λ-vectors. Bathe et al. (Molecular and General Genetics, 252:255–265, 1996) describe a gene library of *C. glutamicum* ATCC13032, which was constructed using the cosmid vector SuperCos I (Wahl et al., 1987, Proceedings of the National Academy of Sciences USA, 84:2160–2164) in *E. coli* K-12 strain NM554 (Raleigh et al., 1988, Nucleic Acids Research 16:1563–1575). Börmann et al. (Molecular Microbiology 6(3), 317–326, 1992)) also describe a gene library of *C. glutamicum* ATCC 13032, using cosmid pHC79 (Hohn and Collins, Gene 11, 291–298 (1980)). A gene library of *C. glutamicum* in *E. coli* may also be produced using plasmids such as pBR322 (Bolivar, Life Sciences, 25, 807–818 (1979)) or pUC9 (Vieira et al., 1982, Gene, 19:259–268). Suitable hosts are in particular those *E. coli* strains with restriction and recombination defects. One example of such a strain is the strain DH5αmcr, which has been described by Grant et al. (Proceedings of the National Academy of Sciences USA, 87 (1990) 4645–4649). The long DNA fragments cloned with the assistance of cosmids may then in turn be sub-cloned in usual vectors suitable for sequencing and then be sequenced, as described, for example, in Sanger et al. (Proceedings of the National Academy of Sciences of the United States of America, 74:5463–5467, 1977).

The novel DNA sequence from *C. glutamicum* that encodes the pfkA gene and is provided by the present invention as SEQ ID NO:1 was obtained in this manner. The amino acid sequence of the corresponding protein was furthermore deduced from the above DNA sequence using the methods described above. SEQ ID NO:2 shows the resultant amino acid sequence of the product of the pfkA gene.

Coding DNA sequences arising from the degeneracy of the genetic code are also provided by the present invention. DNA sequences which hybridise with SEQ ID NO:1 or portions of SEQ ID NO:1 are also provided by the invention.

Conservative substitutions of amino acids in proteins, for example the substitution of glycine for alanine or of aspartic acid for glutamic acid, are known in specialist circles as "sense mutations", which result in no fundamental change in activity of the protein, i.e. they are functionally neutral. It is furthermore known that changes to the N and/or C terminus of a protein do not substantially impair or may even stabilise the function thereof. The person skilled in the art will find information in this connection inter alia in Ben-Bassat et al. (Journal of Bacteriology 169:751–757 (1987)), in O'Regan et al. (Gene 77:237–251 (1989)), in Sahin-Toth et al. (Protein Sciences 3:240–247 (1994)), in Hochuli et al. (Bio/Technology 6:1321–1325 (1988)) and in other standard textbooks of genetics and molecular biology. Amino acid sequences arising in a corresponding manner from SEQ ID NO:2 are also provided by the present invention.

Similarly, DNA sequences which hybridise with SEQ ID NO:1 or portions of SEQ ID NO:1 are also provided by the present invention. Finally, DNA sequences produced by the polymerase chain reaction (PCR) using primers obtained from SEQ ID NO:1 are also provided by the present invention. Such oligonucleotides typically have a length of at least 15 nucleotides.

The person skilled in the art may find instructions for identifying DNA sequences by means of hybridisation inter alia in the manual "The DIG System Users Guide for Filter Hybridization" from Boehringer Mannheim GmbH (Mannheim, Germany, 1993) and in Liebl et al. (International Journal of Systematic Bacteriology (1991) 41: 255–260). The person skilled in the art may find instructions for amplifying DNA sequences using the polymerase chain reaction (PCR) inter alia in the manual by Gait, Oligonucleotide synthesis: a practical approach (IRL Press, Oxford, UK, 1984) and in Newton & Graham, PCR (Spektrum Akademischer Verlag, Heidelberg, Germany, 1994).

The inventors discovered that coryneform bacteria produce L-amino acids, in particular L-lysine, in an improved manner once the pfka has been overexpressed.

Overexpression may be achieved by increasing the copy number of the corresponding genes or by mutating the promoter and regulation region or the ribosome-binding site located upstream from the structural gene. Expression cassettes incorporated upstream from the structural gene act in the same manner. It is additionally possible to increase expression during fermentative L-lysine production by means of inducible promoters. Expression is also improved by measures to extend the lifetime of the mRNA. Enzyme activity is moreover amplified by preventing degradation of the enzyme protein. The genes or gene constructs may either be present in plasmids in a variable copy number or be integrated in the chromosome and amplified. Alternatively, overexpression of the genes concerned may also be achieved by modifying the composition of the nutrient media and culture conditions.

The person skilled in the art will find guidance in this connection inter alia in Martin et al. (Bio/Technology 5, 137–146 (1987)), in Guerrero et al. (Gene 138, 35–41 (1994)), Tsuchiya and Morinaga (Bio/Technology 6, 428–430 (1988)), in Eikmanns et al. (Gene 102, 93–98 (1991)), in European patent EP 0 472 869, in U.S. Pat. No. 4,601,893, in Schwarzer and Pühler (Bio/Technology 9, 84–87 (1991)), in Reinscheid et al. (Applied and Environmental Microbiology 60, 126–132 (1994)), in LaBarre et al. (Journal of Bacteriology 175, 1001–1007 (1993)), in patent application Ser. No. WO 96/15246, in Malumbres et al. (Gene 134, 15–24 (1993)), in Japanese published patent application JP-A-10-229891, in Jensen and Hammer (Biotechnology and Bioengineering 58, 191–195 (1998)), in Makrides (Microbiological Reviews 60:512–538 (1996)) and in known textbooks of genetics and molecular biology.

By way of example, the pfkA gene according to the invention was overexpressed with the assistance of plasmids.

Suitable plasmids are those which are replicated in coryneform bacteria. Numerous known plasmid vectors, such as for example pz1 (Menkel et al., Applied and Environmental Microbiology (1989) 64: 549–554), pEKEx1 (Eikmanns et al., Gene 102:93–98 (1991)) or pHS2-1 et al., Gene 107:69–74 (1991)) are based on the cryptic plasmids pHM1519, pBL1 or pGA1. Other plasmid vectors, such as for example those based on pCG4 (U.S. Pat. No. 4,489,160), or pNG2 (Serwold-Davis et al., FEMS Microbiology Letters 66, 119–124 (1990)), or pAG1 (U.S. Pat. No. 5,158,891) may be used in the same manner.

Further suitable plasmid vectors are those with the assistance of which gene amplification may be performed by integration into the chromosome, as has for example been described by Reinscheid et al. (Applied and Environmental Microbiology 60, 126–132 (1994)) for the duplication or amplification of the hom-thrB operon. In this method, the complete gene is cloned into a plasmid vector which can replicate in a host (typically *E. coli*), but not in *C. glutamicum*. Vectors which may be considered are, for example, pSUP301 (Simon et al., Bio/Technology 1, 784–791 (1983)), pK18mob or pK19mob (Schäfer et al., Gene 145, 69–73 (1994)), pGEM-T (Promega corporation, Madison, Wis., USA), pCR2.1-TOPO (Shuman (1994). Journal of Biological Chemistry 269:32678–84; U.S. Pat. No. 5,487,993), pCR®Blunt (Invitrogen, Groningen, Netherlands; Bernard et al., Journal of Molecular Biology, 234: 534–541 (1993)) or pEM1 (Schrumpf et al, 1991, Journal of Bacteriology 173:4510–4516). The plasmid vector which contains the gene to be amplified is then transferred into the desired strain of *C. glutamicum* by conjugation or transformation. The conjugation method is described, for example, in Schäfer et al. (Applied and Environmental Microbiology 60, 756–759 (1994)). Transformation methods are described, for example, in Thierbach et al. (Applied Microbiology and Biotechnology 29, 356–362 (1988)), Dunican and Shivnan (Bio/Technology 7, 1067–1070 (1989)) and Tauch et al. (FEMS Microbiological Letters 123, 343–347 (1994)). After homologous recombination by means of "crossing over", the resultant strain contains at least two copies of the gene in question.

It may additionally be advantageous for the production of amino acids, in particular L-lysine, to amplify or overexpress not only the pfka gene, but also one or more enzymes of the particular biosynthetic pathway, of glycolysis, of anaplerotic metabolism, of the citric acid cycle or of amino acid export.

For the production of L-lysine, for example, it is thus possible simultaneously to overexpress one or more genes selected from the group the dapA gene which encodes dihydropicolinate synthase (EP-B 0 197 335), or the gap gene which encodes glyceraldehyde-3-phosphate dehydrogenase (Eikmanns (1992), Journal of Bacteriology 174:6076–6086), or the tpi gene which encodes triosephosphate isomerase (Eikmanns (1992), Journal of Bacteriology 174:6076–6086), or the pgk gene which encodes 3-phosphoglycerate kinase (Eikmanns (1992), Journal of Bacteriology 174:6076–6086), or the pyc gene which encodes pyruvate carboxylase (Eikmanns (1992), Journal of Bacteriology 174:6076–6086), or the lysE gene which codes for lysine export (DE-A-195 48 222).

It may furthermore be advantageous for the production of amino acids, in particular L-lysine, in addition to amplifying the pfka gene, simultaneously to attenuate the pck gene which encodes phosphoenolpyruvate carboxykinase (DE 199 50 409.1, DSM 13047) and/or the pgi gene which encodes glucose 6-phosphate isomerase (U.S. Ser. No. 09/396,478, DSM 12969).

It may furthermore be advantageous for the production of amino acids, in particular L-lysine, in addition to overexpressing the pfkA gene, to suppress unwanted secondary reactions (Nakayama: "Breeding of Amino Acid Producing Micro-organisms", in: Overproduction of Microbial Products, Krumphanzl, Sikyta, Vanek (eds.), Academic Press, London, UK, 1982).

For the purposes of amino acid production, in particular of L-lysine, the microorganisms produced according to the invention may be cultured continuously or discontinuously using the batch process or the fed batch process or repeated fed batch process. A summary of known culture methods is given in the textbook by Chmiel (Bioprozesstechnik 1. Einführung in die Bioverfahrenstechnik (Gustav Fischer Verlag, Stuttgart, 1991)) or in the textbook by Storhas (Bioreaktoren und periphere Einrichtungen (Vieweg Verlag, Braunschweig/Wiesbaden, 1994)).

The culture medium to be used must adequately satisfy the requirements of the particular strains. Culture media for various microorganisms are described in "Manual of Methods for General Bacteriology" from the American Society for Bacteriology (Washington D.C., USA, 1981). Carbon sources which may be used are sugars and carbohydrates, such as glucose, sucrose, lactose, fructose, maltose, molasses, starch and cellulose for example, oils and fats, such as soya oil, sunflower oil, peanut oil and coconut oil for example, fatty acids, such as palmitic acid, stearic acid and linoleic acid for example, alcohols, such as glycerol and ethanol for example, and organic acids, such as acetic acid for example. These substances may be used individually or as a mixture. Nitrogen sources which may be used comprise organic compounds containing nitrogen, such as peptones, yeast extract, meat extract, malt extract, corn steep liquor, soya flour and urea or inorganic compounds, such as ammonium sulfate, ammonium chloride, ammonium phosphate, ammonium carbonate and ammonium nitrate. The nitrogen sources may be used individually or as a mixture. Phosphorus sources which may be used are phosphoric acid, potassium dihydrogen phosphate or dipotassium hydrogen phosphate or the corresponding salts containing sodium. The culture medium has additionally to contain salts of metals, such as magnesium sulfate or iron sulfate for example, which are necessary for growth. Finally, essential growth-promoting substances such as amino acids and vitamins may also be used in addition to the above-stated substances. Suitable precursors may furthermore be added to the culture medium. The stated feed substances may be added to the culture as a single batch or be fed appropriately during culturing.

Basic compounds, such as sodium hydroxide, potassium hydroxide, ammonia or ammonia water, or acidic compounds, such as phosphoric acid or sulfuric acid, are used appropriately to control the pH of the culture. Foaming may be controlled by using antifoaming agents such as fatty acid polyglycol esters for example. Plasmid stability may be maintained by the addition to the medium of suitable selectively acting substances, for example antibiotics. Oxygen or oxygen-containing gas mixtures, such as air for example, are introduced into the culture in order to maintain aerobic conditions. The temperature of the culture is normally from 20 C. to 45° C. and preferably from 25° C. to 40° C. The culture is continued until the maximum quantity of lysine has formed. This aim is normally achieved within 10 to 160 hours.

Analysis of L-lysine may be performed by anion exchange chromatography with subsequent ninhydrin derivatisation, as described in Spackman et al. (Analytical Chemistry, 30, (1958), 1190).

The purpose of the process according to the invention is the fermentative production of amino acids, in particular L-lysine.

BRIEF DESCRIPTION OF THE DRAWINGS

FIG. 1: Map of plasmid pT-pfkAexp

FIG. 2: Map of plasmid pT-pfkAexp

The abbreviations and names are defined as follows.

| Tet: | Resistance gene for tetracycline. |
|---|---|
| oriV: | Plasmid-code replication origin of *E. coli* |
| RP4mob: | mob region for plasmid mobilisation |
| rep: | Plasmid-coded replication origin from *C. glutamicum* plasmid pGA1 |
| per: | Gene for controlling copy number from pGA1 |
| lacZ-alpha: | lacZα gene fragment (*N* terminus) of the β-galactosidase gene |
| 'lacZa': | 5' end of the lacZα gene fragment |
| lacZ-alpha': | 3' end of the lacZα gene fragment |
| pfkA: | pfkA gene from *C. glutamicum* ATCC13032 |
| BamHI: | Restriction site of the restriction enzyme BamHI |
| EcoRI: | Restriction site of the restriction enzyme EcoRI |
| HindIII: | Restriction site of the restriction enzyme HindIII |
| KpnI: | Restriction site of the restriction enzyme KpnI |
| PstI: | Restriction site of the restriction enzyme PstI |
| PvuI: | Restriction site of the restriction enzyme PvuI |
| SalI: | Restriction site of the restriction enzyme SalI |
| SacI: | Restriction site of the restriction enzyme SacI |
| SmaI: | Restriction site of the restriction enzyme SmaI |
| SphI: | Restriction site of the restriction enzyme SphI |
| XbaI: | Restriction site of the restriction enzyme XbaI |
| XhoI: | Restriction site of the restriction enzyme XhoI |

DETAILED DESCRIPTION OF THE INVENTION

The present invention is illustrated in greater detail by the following practical examples.

EXAMPLE 1

Production of a genomic cosmid gene library from *Corynebacterium glutamicum* ATCC13032

Chromosomal DNA from *Corynebacterium glutamicum* ATCC 13032 was isolated as described in Tauch et al., (1995, Plasmid 33:168–179) and partially cleaved with the restriction enzyme Sau3AI (Amersham Pharmacia, Freiburg, Germany, product description Sau3AI, code no. 27-0913-02). The DNA fragments were dephosphorylated with shrimp alkaline phosphatase (Roche Molecular Biochemicals, Mannheim, Germany, product description SAP, code no. 1758250). The DNA of cosmid vector Super-Cosl (Wahl et al. (1987) Proceedings of the National Academy of Sciences USA 84:2160–2164), purchased from Stratagene (La Jolla, USA, product description SuperCosl Cosmid Vector Kit, code no. 251301) was cleaved with the restriction enzyme XbaI (Amersham Pharmacia, Freiburg, Germany, product description XbaI, code no. 27-0948-02) and also dephosphorylated with shrimp alkaline phosphatase. The cosmid DNA was then cleaved with the restriction enzyme BamHI (Amersham Pharmacia, Freiburg, Germany, product description BamHI, code no. 27-0868-04). Cosmid DNA treated in this manner was mixed with the treated ATCC 13032 DNA and the batch was treated with T4 DNA ligase (Amersham Pharmacia, Freiburg, Germany, product description T4 DNA Ligase, code no. 27-0870-04). The ligation mixture was then packed in phages using Gigapack II XL Packing Extracts (Stratagene, La Jolla, USA, product description Gigapack II XL Packing Extract, code no. 200217). *E. coli* strain NM554 (Raleigh et al. 1988, Nucleic Acid Res. 16:1563–1575) was infected by suspending the cells in 10 mM $MgSO_4$ and mixing them with an aliquot of the phage suspension. The cosmid library was infected and titred as described in Sambrook et al. (1989, Molecular Cloning: A laboratory Manual, Cold Spring Harbor), the cells being plated out on LB agar (Lennox, 1955, Virology, 1:190) with 100 μg/ml of ampicillin. After overnight incubation at 37° C., individual recombinant clones were selected.

EXAMPLE 2

Isolation and Sequencing of the pfkA Gene

Cosmid DNA from an individual colony was isolated in accordance with the manufacturer's instructions using the Qiaprep Spin Miniprep Kit (product no. 27106, Qiagen, Hilden, Germany) and partially cleaved with the restriction enzyme Sau3AI (Amersham Pharmacia, Freiburg, Germany, product description Sau3AI, product no. 27-0913-02). The DNA fragments were dephosphorylated with shrimp alkaline phosphatase (Roche Molecular Biochemicals, Mannheim, Germany, product description SAP, product no. 1758250). Once separated by gel electrophoresis, the cosmid fragments of a size of 1500 to 2000 bp were isolated using the QiaExII Gel Extraction Kit (product no. 20021, Qiagen, Hilden, Germany). The DNA of the sequencing vector pZero-1 purchased from Invitrogen (Groningen, Netherlands, product description Zero Background Cloning Kit, product no. K2500-01) was cleaved with the restriction enzyme BamHI (Amersham Pharmacia, Freiburg, Germany, product description BamHI, product no. 27-0868-04). Ligation of the cosmid fragments into the sequencing vector pZero-1 was performed as described by Sambrook et al. (1989, Molecular Cloning: A laboratory Manual, Cold Spring Harbor), the DNA mixture being incubated overnight with T4 ligase (Pharmacia Biotech, Freiburg, Germany). This ligation mixture was then electroporated into the *E. coli* strain DH5αMCR (Grant, 1990, Proceedings of the National Academy of Sciences U.S.A., 87:4645–4649) (Tauch et al. 1994, FEMS Microbiol Letters, 123:343–7) and plated out onto LB agar (Lennox, 1955, Virology, 1:190) with 50 μg/ml of Zeocin. Plasmids of the recombinant clones were prepared using the Biorobot 9600 (product no. 900200, Qiagen, Hilden, Germany). Sequencing was performed using the dideoxy chain termination method according to Sanger et al. (1977, Proceedings of the National Academy of Sciences U.S.A., 74:5463–5467) as modified by Zimmermann et al. (1990, Nucleic Acids Research, 18:1067). The "RR dRhodamin Terminator Cycle Sequencing Kit" from PE Applied Biosystems (product no. 403044, Weiterstadt, Germany) was used.

Separation by gel electrophoresis and analysis of the sequencing reaction was performed in a "Rotiphorese NF" acrylamide/bisacrylamide gel (29:1) (product no. A124.1, Roth, Karlsruhe, Germany) using the "ABI Prism 377" sequencer from PE Applied Biosystems (Weiterstadt, Germany).

The resultant raw sequence data were then processed using the Staden software package (1986, Nucleic Acids Research, 14:217–231), version 97-0. The individual sequences of the p-zero 1 derivatives were assembled into a cohesive contig. Computer-aided coding range analysis was performed using XNIP software (Staden, 1986, Nucleic Acids Research, 14:217–231). Further analysis was performed using the "BLAST search programs" (Altschul et al., 1997, Nucleic Acids Research, 25:3389–3402), against the non-redundant database of the "National Center for Biotechnology Information" (NCBI, Bethesda, Md., USA).

The resultant nucleotide sequence is shown as SEQ ID NO:1. Analysis of the nucleotide sequence revealed an open reading frame of 1029 base pairs, which was designated the pfkA gene. The pfka gene encodes a protein of 343 amino acids.

EXAMPLE 3

Production of a Plasmid for Overexpressing pfka in *Corynebacterium glutamicum*

3.1. Cloning of pfka in the pCR2-Blunt Vector

Chromosomal DNA from *Corynebacterium glutamicum* ATCC 13032 was isolated as described in Tauch et al., (1995, Plasmid 33:168–179). On the basis of the sequence of the pfkA gene for *C. glutamicum* known from Example 2, the following oligonucleotides were selected for the polymerase chain reaction:

pfka-exp'
    5'-AAC TGC AGC TCT GGC GAT TA-3' (SEQ ID NO:3)

pfk-ex2
    5'-AAC TAT CCA AAC ATT GCC TG-3' (SEQ ID NO:4)

These primers were synthesised by the company MWG Biotech (Ebersberg, Germany) and the PCR reaction performed in accordance with the standard PCR method of Innis et al. (PCR protocols. A guide to methods and applications, 1990, Academic Press) using Pwo polymerase from Roche Diagnostics GmbH (Mannheim, Germany). A DNA fragment of approx. 1160 bp in size, which bears the pfkA gene, was isolated with the assistance of the polymerase chain reaction.

The amplified DNA fragment was ligated into the vector pCR2 Blunt Vector (Bernard et al., (1983) Journal of Molecular Biology. 234:534–541) using the Zero Blunt PCR Cloning Kit from Invitrogen Corporation (Carlsbad, Calif., USA; catalogue number K2700-20). The *E. coli* strain Top10F (Grand et al. (1990) Proceedings of the National Academy of Sciences, USA. 87:4645–4649) was transformed with the ligation batch. Plasmid-bearing cells were selected by plating the transformation batch out onto LB agar (Sambrook et al., Molecular cloning: a laboratory manual. $2^{nd}$ Ed. Cold Spring Harbor Laboratory Press, Cold Spring Harbor, N.Y.) which had been supplemented with 50 mg/l of kanamycin. Plasmid DNA was isolated from a transformant using the QIAprep Spin Miniprep Kit from Qiagen and verified by restriction with the restriction enzyme EcoRI and subsequent agarose gel electrophoresis (0.8%). The plasmid was named pCRB1-pfkAexp1.

3.2. Production of the Shuttle Vector pEC-T18mob2

The *E. coli-C. glutamicum* shuttle vector was constructed in accordance with the prior art. The vector contains the replication region rep of plasmid PGA1, including the replication effector per (U.S. Pat. No. 5,175,108; Nesvera et al., Journal of Bacteriology 179, 1525–1532 (1997)), the tetA(Z) gene, which imparts tetracycline resistance, of plasmid pAG1 (U.S. Pat. No. 5,158,891; gene library entry at the National Center for Biotechnology Information (NCBI, Bethesda, Md., USA) with the accession number AF121000), the replication origin oriV of plasmid pMB1 (Sutcliffe, Cold Spring Harbor Symposium on Quantitative Biology 43, 77–90 (1979)), the lacZα gene fragment including the lac promoter and a multiple cloning site (mcs) (Norrander et al. Gene 26, 101–106 (1983)) and the mob region of plasmid RP4 (Simon et al., (1983) Bio/Technology 1:784–791). The constructed vector was then transformed into *E. coli* strain DH5α (Hanahan, in: DNA cloning. A practical approach. Vol. I. IRL-Press, Oxford, Washington D.C., USA). Plasmid-bearing cells were selected by plating the transformation batch out onto LB agar (Sambrook et al., Molecular cloning: a laboratory manual. $2^{nd}$ Ed. Cold Spring Harbor Laboratory Press, Cold Spring Harbor, N.Y.) which had been supplemented with 5 mg/l of tetracycline. Plasmid DNA was isolated from a transformant using the QIAprep Spin Miniprep Kit from Qiagen and verified by restriction with the restriction enzymes EcoRI and HindIII and subsequent agarose gel electrophoresis (0.8%). The plasmid was named pEC-T18mob2 and is shown in FIG. 1.

3.3. Cloning of pfkA into Shuttle Vector pEC-T18mob2

The vector used was the *E. coli-C. glutamicum* shuttle vector pEC-T18mob2 described in Example 3.2. DNA from this plasmid was completely cleaved with the restriction enzyme EcoRI and then dephosphorylated with shrimp alkaline phosphatase (Roche Molecular Biochemicals, Mannheim, Germany, product description SAP, product no. 1758250).

The pfkA gene was isolated from the plasmid pCRB1-pfkAexp1 described in Example 3.1. by complete cleavage with the enzyme EcoRI. The approx. 1160 bp pfkA fragment was isolated from the agarose gel using the QiaExII Gel Extraction Kit (product no. 20021, Qiagen, Hilden, Germany).

The pfkA fragment obtained in this manner was mixed with the prepared pEC-T18mob2 vector and the batch was treated with T4 DNA ligase (Amersham Pharmacia, Freiburg, Germany, product description T4 DNA Ligase, code no. 27-0870-04). The ligation batch was then transformed into *E. coli* strain DH5α (Hanahan, in: DNA cloning. A practical approach. Vol. I. IRL-Press, Oxford, Washington D.C., USA). Plasmid-bearing cells were selected by plating the transformation batch out onto LB agar (Lennox, 1955, Virology, 1:190) with 5 mg/l of tetracycline. After overnight incubation at 37° C., individual recombinant clones were selected. Plasmid DNA was isolated from a transformant in accordance with the manufacturer's instructions using the Qiaprep Spin Miniprep Kit (product no. 27106, Qiagen, Hilden, Germany) and cleaved with the restriction enzyme EcoRI in order to check the plasmid by subsequent agarose gel electrophoresis. The resultant plasmid was named pT-pfkAexp. It is shown in FIG. 2.

EXAMPLE 4

Transformation of Strain DSM5715 with Plasmid pT-pfkAexp

Strain DSM5715 (EP-B-0 435 132) was then transformed with plasmid pT-pfkAexp using the electroporation method described by Liebl et al. (FEMS Microbiology Letters, 53:299–303 (1989)). Transformant selection proceeded on LBHIS agar consisting of 18.5 g/l of brain-heart infusion bouillon, 0.5 M sorbitol, 5 g/l of Bacto tryptone, 2.5 g/l of Bacto yeast extract, 5 g/l of NaCl and 18 g/l of Bacto agar, which had been supplemented with 5 mg/l of tetracycline. Incubation was performed for 2 days at 33° C.

Plasmid DNA was isolated from a transformant using the conventional methods (Peters-Wendisch et al., 1998, Microbiology, 144, 915–927), cut with the restriction endonuclease EcoRI in order to check the plasmid by subsequent agarose gel electrophoresis. The resultant strain was named DSM5715/pT-pfkAexp.

EXAMPLE 5

Production of Lysine

The *C. glutamicum* strain DSM5715/pT-pfkAexp obtained in Example 4 was cultured in a nutrient medium suitable for the production of lysine and the lysine content of the culture supernatant was determined.

To this end, the strain was initially incubated for 24 hours at 33° C. on an agar plate with the appropriate antibiotic (brain/heart agar with tetracycline (5 mg/l)). Starting from this agar plate culture, a preculture was inoculated (10 ml of medium in a 100 ml Erlenmeyer flask). The medium used for the preculture was complete medium CgIII (2.5 g/l of NaCl, 10 g/l of Bacto peptone, 10 g/l of Bacto yeast extract, 20 g/l of glucose, pH 7.4). Tetracycline (5 mg/l) was added to this medium. The preculture was incubated for 16 hours at 33° C. on a shaker at 240 rpm. A main culture was inoculated from this preculture, such that the initial OD (660 nm) of the main culture was 0.1. Medium MM was used for the main culture.

| Medium MM | |
|---|---|
| CSL (Corn Steep Liquor) | 5 g/l |
| MOPS (Morpholinopropanesulfonic acid) | 20 g/l |
| Glucose (separately autoclaved) | 50 g/l |
| $(NH_4)_2SO_4$ | 25 g/l |
| $KH_2PO_4$ | 0.1 g/l |
| $MgSO_4 * 7 H_2O$ | 1.0 g/l |
| $CaCl_2 * 2 H_2O$ | 10 mg/l |
| $FeSO_4 * 7 H_2O$ | 10 mg/l |
| $MnSO_4 * H_2O$ | 5.0 mg/l |
| Biotin (sterile-filtered) | 0.3 mg/l |
| Thiamine * HCl (sterile-filtered) | 0.2 mg/l |
| L-leucine (sterile-filtered) | 0.1 g/l |
| $CaCO_3$ | 25 g/l |

CSL, MOPS and the salt solution were adjusted to pH 7 with ammonia water and autoclaved. The sterile substrate and vitamin solutions, together with the dry-autoclaved $CaCO_3$ are then added.

Culturing is performed in a volume of 10 ml in a 100 ml Erlenmeyer flask with flow spoilers. Kanamycin (25 mg/l) was added. Culturing was performed at 33° C. and 80% atmospheric humidity.

After 24 hours, the OD was determined at a measurement wavelength of 660 nm using a Biomek 1000 (Beckmann Instruments GmbH, Munich). The quantity of lysine formed was determined using an amino acid analyser from Eppendorf-BioTronik (Hamburg, Germany) by ion exchange chromatography and post-column derivatisation with ninhydrin detection.

Table 1 shows the result of the test.

TABLE 1

| Strain | OD(660) | Lysine HCl g/l |
|---|---|---|
| DSM5715/pT-pfkAexp | 14.6 | 10.1 |
| DSM5715 | 15.2 | 8.1 |

What is claimed is:

1. An isolated polynucleotide of comprising a nucleotide sequence encoding a protein with an amino acid sequence as set forth in SEQ ID NO:2, wherein the polynucleotide encodes a polypeptide having phosphofructokinase enzymatic activity.

2. An isolated polynucleotide comprising a nucleotide sequence that is at least 90% identical to that of SEQ ID NO:1 encoding a protein with an amino acid sequence of SEQ ID NO:2 and wherein said protein has phosphofructokinase enzymatic activity.

3. An isolated polynucleotide comprising a nucleotide sequence that is at least 95% identical to that of SEQ ID NO:1 encoding a protein with an amino acid sequence of SEQ ID NO:2 and wherein said protein has phosphofructokinase enzymatic activity.

4. An isolated polynucleotide comprising the nucleotide sequence of nucleotides 143–1171 of SEQ ID NO:1, wherein the polynucleotide encodes a polypeptide having phosphofructokinase enzymatic activity.

5. An isolated polynucleotide comprising the nucleotide sequence of SEQ ID NO:1, wherein the polynucleotide encodes a polypeptide having phosphofructokinase enzymatic activity.

6. A vector comprising the polynucleotide of any one of claims 1 or 2–5.

7. The vector of claim 6, wherein said vector is a plasmid.

8. A bacterial host cell transformed with the vector of claim 7.

9. The bacterial host cell of claim 8, wherein said bacterial host cell is of the species *Corynebacterium glutamicum*.

* * * * *